United States Patent
Nazareth et al.

(10) Patent No.: US 10,001,449 B2
(45) Date of Patent: Jun. 19, 2018

(54) SYSTEMS, DEVICES AND METHODS FOR A HYDROSCOPIC BASED LATERAL FLOW ASSAY

(71) Applicant: Church & Dwight, Co., Inc., Princeton, NJ (US)

(72) Inventors: Albert Nazareth, Mercerville, NJ (US); Shang Li, Princeton Junction, NJ (US); Timothy Snowden, Howell, NJ (US); Giles H. W. Sanders, Hertfordshire (GB); Anthony Cass, Hertfordshire (GB)

(73) Assignee: Church & Dwight Co., Inc., Princeton, NJ (US)

( * ) Notice: Subject to any disclaimer, the term of this patent is extended or adjusted under 35 U.S.C. 154(b) by 136 days.

(21) Appl. No.: 14/570,913

(22) Filed: Dec. 15, 2014

(65) Prior Publication Data
US 2016/0169881 A1  Jun. 16, 2016

(51) Int. Cl.
| G01N 27/02 | (2006.01) |
| G01N 33/543 | (2006.01) |
| G01N 33/558 | (2006.01) |

(52) U.S. Cl.
CPC ......... *G01N 27/02* (2013.01); *G01N 33/5438* (2013.01); *G01N 33/558* (2013.01)

(58) Field of Classification Search
None
See application file for complete search history.

(56) References Cited

U.S. PATENT DOCUMENTS

| 5,607,863 A | 3/1997 | Chandler et al. |
| 6,319,676 B1 | 11/2001 | Nazareth et al. |
| 7,300,802 B2 | 11/2007 | Paek et al. |
| 7,678,256 B2 * | 3/2010 | Davalos ............ B03C 5/005 204/547 |
| 2003/0129680 A1 | 7/2003 | O'Connor |
| 2003/0180815 A1 | 9/2003 | Rawson et al. |
| 2003/0203498 A1 | 10/2003 | Neel et al. |
| 2006/0008896 A1 | 1/2006 | Nazareth et al. |
| 2007/0172878 A1 | 7/2007 | Akhavan-Tafti et al. |
| 2007/0224625 A1 | 9/2007 | Hainfeld et al. |
| 2008/0076169 A1 | 3/2008 | Miles et al. |
| 2008/0083618 A1 | 4/2008 | Neel et al. |

(Continued)

FOREIGN PATENT DOCUMENTS

| WO | 2013/083686 A1 | 5/2013 |
| WO | 2013116333 A2 | 8/2013 |

OTHER PUBLICATIONS

Non-Final Office Action for U.S. Appl. No. 14/570,973, pp. 1-45, dated May 5, 2016.

(Continued)

*Primary Examiner* — Paresh Patel
(74) *Attorney, Agent, or Firm* — Church & Dwight Co., Inc.

(57) ABSTRACT

Systems, methods, and test kits for detecting and quantifying an analyte level in a biological fluid sample using impedance measurements, are disclosed. The fluid sample is applied to a lateral flow strip, and impedance of the strip is measured as the assay dries. Analysis of the drying-dependent impedance measurements indicates the presence and quantity of the analyte in the fluid sample.

11 Claims, 9 Drawing Sheets

(56) References Cited

U.S. PATENT DOCUMENTS

| | | |
|---|---|---|
| 2008/0105565 A1 | 5/2008 | Davalos et al. |
| 2008/0145835 A1 | 6/2008 | Alajem et al. |
| 2008/0273918 A1 | 11/2008 | Linder et al. |
| 2009/0180929 A1 | 7/2009 | Petruno et al. |
| 2010/0099112 A1 | 4/2010 | Zhou et al. |
| 2010/0099114 A1 | 4/2010 | Wu |
| 2010/0267065 A1 | 10/2010 | Geiger et al. |
| 2011/0192726 A1* | 8/2011 | Chen .................. G01N 33/5438 204/547 |
| 2012/0070822 A1 | 3/2012 | Bae et al. |
| 2012/0107851 A1 | 5/2012 | Killard et al. |
| 2013/0280696 A1 | 10/2013 | Millenson et al. |
| 2014/0113384 A1 | 4/2014 | Kavusi et al. |
| 2014/0273187 A1 | 9/2014 | Johnson et al. |
| 2016/0169887 A1* | 6/2016 | Nazareth .............. G01N 33/558 436/501 |

OTHER PUBLICATIONS

PCT International Search Report and Written Opinion for PCT/US/62989, pp. 1-12, dated Mar. 28, 2016.

Kaur, et al., "Immunochromatographic Dipstick Assay Format Using Gold Nanoparticles Labeled Protein-Hapten Conjugate for the Detection of Atrazine", Environmental Science & Technology, vol. 41, No. 14. 2007, pp. 5028-5036.

Invitation to Pay Additional Fees and, Where Applicable, Protest Fee for PCT/US15/62989, dated Jan. 28, 2016, pp. 1-2.

PCT International Search Report and Written Opinion for PCT/US15/62979, dated Feb. 4, 2016, pp. 1-8.

* cited by examiner

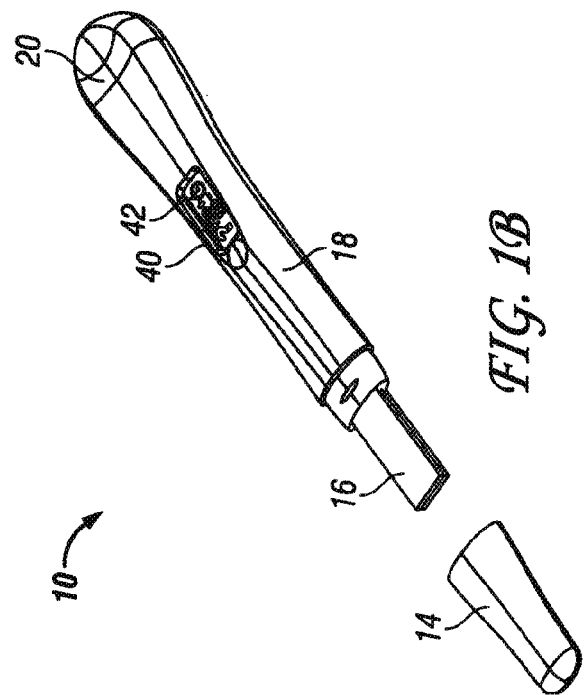
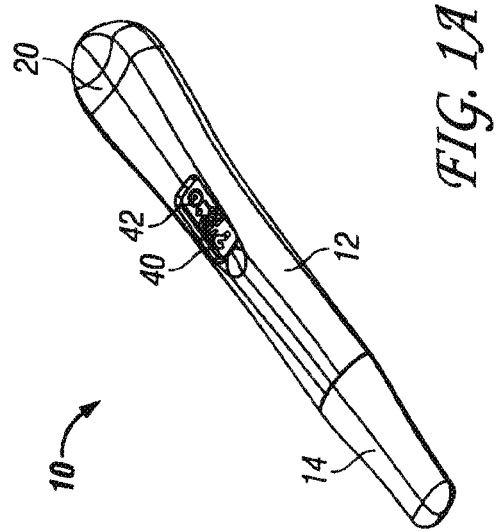
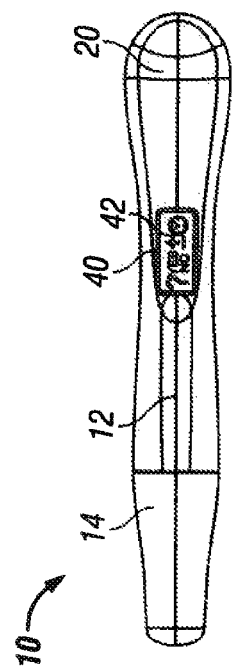

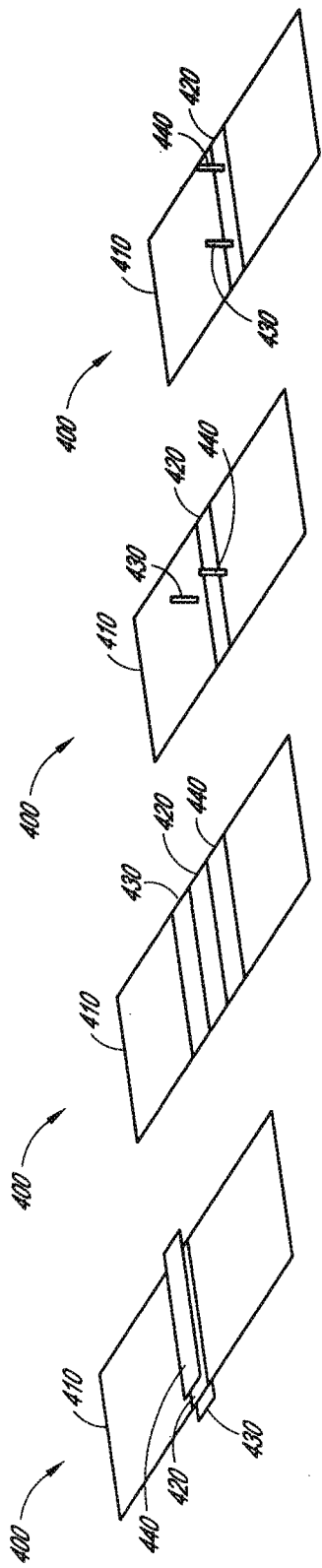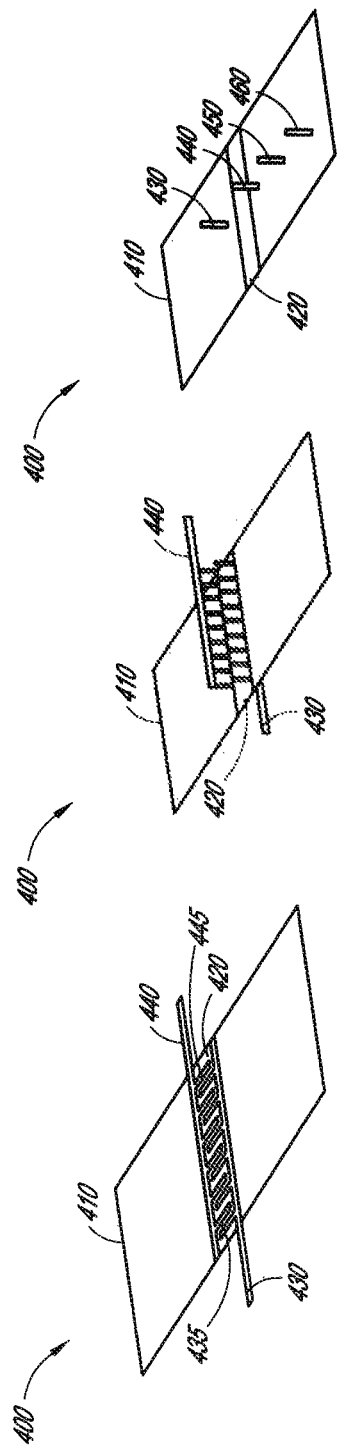

SYSTEMS, DEVICES AND METHODS FOR A HYDROSCOPIC BASED LATERAL FLOW ASSAY

BACKGROUND

Field of the Invention

The present invention relates to diagnostic assays for analytes in a liquid sample. In some embodiments, methods and devices for the detection of an analyte in a body fluid using, impedance are provided.

Description of the Related Art

Many types of ligand-receptor assays have been used to detect the presence of analytes in body fluids such as saliva, urine or blood. These assays typically involve antigen-antibody reactions, synthetic conjugates comprising enzymatic, fluorescent, or visually observable tags, and specially designed reactor chambers. In most of these assays, there is a receptor (e.g., an antibody) specific for the selected analyte (e.g., antigen), and a means for detecting the presence and/or amount of the antigen-antibody reaction product. Although some commercially available tests are designed to a quantitative determination, in many circumstances all that is required is a qualitative indication (e.g., positive/negative). Examples of such qualitative assays include blood typing, pregnancy testing, ovulation prediction and many types of urinalysis.

Diagnostic assays should generally be very sensitive because of the often low concentrations of analytes of interest, present in a test fluid. False positives can be problematic particularly with agglutination and other rapid detection methods such as dipstick and color change tests. Because of these problems, sandwich assays which use metal sols or other types of colored particles have been developed that rely on the interaction between avidin and biotin-tagged antibodies. For example, in some commercially available pregnancy tests, an antibody-antigen sandwich complex comprising a colloidal gold-labeled anti-hCG antibody and an anti-hCG biotin-labeled antibody is used. Test strips of this nature are known in the art, and are described in more detail in, for example, FIGS. 2-6 and the accompanying description of U.S. Pat. No. 6,319,676, the content of which is hereby incorporated by reference in its entirety.

Other proposals have sought to exploit the changes in impedance that occur due to the presence of metal-labeled antibodies. For example, International Application Publication No. WO2013/083686, the content of which is herein incorporated by reference in its entirety, discloses electrodes located on test and reference regions measuring changes in capacitance. A difference in capacitance between the test and reference regions is indicative of the presence and quantity of a bound metal and thus of the target analyte. However, in such systems the changes in the capacitance are small, and the layout thus requires precision. This requires more precise tools and other improvements to the designing, building and assembling of such devices. Thus, burdensome constraints are imposed on production, driving up costs for end users. Therefore, it is desirable to have further improvements in the design, reliability, and ease of manufacture for impedance-based assays and to provide the market with affordable test kits.

SUMMARY

In one aspect, a device for detecting an analyte in a fluid sample is disclosed. In some embodiments, the device comprises a strip comprising a sample receiving region configured to receive the fluid sample, a capture region, and a non-capture region. In some embodiments, the strip is configured such that when a fluid sample is applied to the sample receiving region, the fluid sample flows laterally to the capture region and the non-capture region. In some embodiments, the device further comprises a plurality of electrodes at least partially aligned with the capture region, a plurality of electrodes at least partially aligned with the non-capture region, and an electronic circuit comprising a processor coupled to the electrodes, with the processor configured to execute a set of instructions to perform a method for detecting the analyte in the fluid sample. In some embodiments, the method comprises measuring a drying-dependent impedance difference between the capture region and the non-capture region.

In some embodiments the measuring of a drying-dependent impedance difference comprises measuring the drying-dependent impedance difference over a drying time period, wherein the drying time period comprises a length of time sufficient for the impedance difference to reach a maximum.

In some embodiments, the method further comprises analyzing the impedance difference over the drying time period, and determining whether the analyte is present in the fluid sample based in part on the analysis of the impedance difference. In some embodiments, measuring the drying-dependent impedance difference between the capture region and the non-capture region comprises measuring afirst impedance of the capture region, measuring a second impedance of the non-capture region and determining a first impedance difference based on subtracting the first impedance from the second impedance. In some embodiments, measuring the drying-dependent impedance difference between the capture region and the non-capture region further comprises measuring the first impedance of the capture region at a first time and measuring the second impedance of the non-capture region at the first time.

In some embodiments, the method further comprises comparing a test impedance difference with a threshold impedance difference, wherein presence of an analyte in the fluid sample is indicated when the test rimpedance difference is greater than the threshold impedance difference, sand wherein the test impedance difference is the first impedance difference as a percentage of the second impedance of the non-capture region. In some embodiments, the threshold impedance difference is 20%.

In some embodiments, measuring the drying-dependent impedance difference over a drying time period further comprises calculating drying rates of the capture and non-capture regions. In some embodiments, the drying rates indicate the presence and/or a quantity of the analyte in the fluid sample. In some embodiments calculating the drying rates comprises, measuring a first impedance of the capture region at a first time, measuring a second impedance of the non-capture region at the first time, measuring a third impedance of the capture region at a second time later than the first time, measuring a fourth impedance of the non-capture region at the second time, determining a first impedance difference based on subtracting the first impedance from the third, impedance, determining a second impedance difference based on subtracting the second impedance from the fourth impedance, determining a time difference based on subtracting the first time from the second time, determining a capture region drying rate based on dividing the first impedance difference by the time difference and determining a non-capture region drying rate based on dividing the second impedance difference by the time difference.

In some embodiments, the method further comprises measuring the impedance difference over a range of frequencies. In some embodiments the range of frequencies is 1 KHz to 100 Khz.

In some embodiments the device further comprises a mechanism for drying the capture region and, the non-capture region. In some embodiments the mechanism for drying is an ambient air valve. In some embodiments, the mechanism for drying is a drying element. In some embodiments, the drying element is a heating element. In some embodiments, the mechanism for drying is a mechanical press. In some embodiments, the mechanical press is a sponge.

In some embodiments, at least two of the electrodes are positioned along the capture region. In some embodiments, at least two of the electrodes are positioned along the non-capture region. In some embodiments, at least two of the electrodes are positioned across the capture region. In some embodiments, at least two of the electrodes are positioned across the non-capture region.

In some embodiments, the strip further comprises a first antibody region comprising a first antibody that recognizes an epitope of the analyte, and a second antibody region comprising a second antibody that recognizes a different epitope of the analyte. In some embodiments, the first antibody is bound to a first label, and the second antibody is bound to a second label. In some embodiments, the first antibody is an anti-hCG antibody, and wherein the second antibody is also an anti-hCG antibody that recognizes a different epitope of an hCG molecule. In some embodiments, the first label is gold. In some embodiments, the first label is silver. In some embodiments, the first label is a polymer. In some embodiments, the second label is biotin.

In some embodiments, the capture region comprises an immobilized capture agent that captures the analyte. The immobilized capture agent may capture the analyte directly or indirectly. In some embodiments, the immobilized capture agent is streptavidin. In some embodiments, the immobilized capture agent is monomeric or polymeric avidin In some embodiments, the non-capture region is configured to not capture the analyte.

In some embodiments, the strip further comprises a release medium, a capture medium, an absorbent medium and a backing. In some embodiments, the release medium comprises the sample receiving region, a first antibody region comprising a first antibody that recognizes an epitope of the analyte, and a second antibody region comprising a second antibody that recognizes a different epitope of the analyte. In some embodiments, the capture medium comprises the capture region. In some embodiments, the capture medium comprises a control region. In some embodiments, the release medium is cellulosic. In some embodiments, the capture medium is nitrocellulose membrane. In some embodiments, the absorbent medium is absorbent paper. In some embodiments, the backing is mylar.

In some embodiments, the device further comprises a control region of the strip, wherein the strip is further configured such that when a fluid sample is applied to the sample receiving region, the fluid sample flows laterally to the control region, a plurality of electrodes at least partially aligned with the control region, and the method further comprises measuring impedances of the control region over the drying time period.

In another aspect, a method for detecting an analyte in a fluid sample is disclosed. In some embodiments, the method comprises applying a fluid sample to a strip, wherein the strip is configured such that the fluid sample flows laterally to a capture region and a non-capture region of the strip, and measuring a drying-dependent impedance difference between the capture region and the non-capture region.

In some embodiments, the method further comprises measuring the drying-dependent impedance difference over a drying time period, wherein the drying time period comprises a length of time sufficient for the impedance difference to reach a maximum.

In some embodiments, the method further comprises analyzing the impedance difference over the drying time period, and determining whether the analyte is present in the fluid sample based in part on the analysis of the impedance difference. In some embodiments, measuring the drying-dependent impedance difference between the capture region and the non-capture region comprises measuring a first impedance of the capture region, measuring a second impedance of the non-capture region and determining a first impedance difference by subtracting the first impedance from the second impedance. In some embodiments, measuring the drying-dependent impedance difference between the capture, region and the non-capture region further comprises measuring the first impedance of the capture region at a first time and measuring the second impedance of the non-capture region at the first time.

In some embodiments, the method further comprises comparing a test impedance difference with a threshold impedance difference, wherein presence of an analyte in the fluid sample is indicated when the test impedance difference is greater than the threshold impedance difference, and wherein the test impedance difference is the first impedance difference as a percentage of the second impedance of the non-capture region. In some embodiments, the threshold impedance difference is 20%.

In some embodiments, measuring, the drying-dependent impedance difference over a drying time period further comprises calculating drying rates of the capture and non-capture regions. In, some embodiments, the drying rates indicate the presence and/or a quantity of the analyte in the fluid sample. In, some embodiments, calculating the drying rates comprises measuring a first impedance of the capture region at a first time, measuring a second impedance of the non-capture region at the first time, measuring a third impedance of the capture region at a second time later than the first time, measuring a fourth impedance of the non-capture region at the second time, determining a first impedance difference by subtracting the first impedance from the third impedance, determining a second impedance difference by subtracting the second impedance from the fourth impedance, determining a time difference by subtracting the first time from the second time, determining a capture region drying rate by dividing the first impedance difference by the time difference and determining a non-capture region drying rate by dividing the second impedance difference by the time difference.

In some embodiments, the method further comprises measuring the impedance difference over a range of frequencies.

In some embodiments, the method further comprises drying the capture region and the non-capture region.

In some embodiments, the strip is further configured such that the fluid sample flows laterally to the control region and the method further comprises measuring impedances of the control region of the strip over the drying time period.

BRIEF DESCRIPTION OF THE DRAWINGS

FIGS. 1A-1C show different views of an embodiment of a drying-dependent impedance-based assay device with a digital display.

FIGS. 4A-4G show perspective views of various embodiments of electrode layouts about a measurement region on a membrane that may be part of a test strip in a drying-dependent impedance-based assay device.

DETAILED DESCRIPTION OF THE PREFERRED EMBODIMENT

Figure 2A:
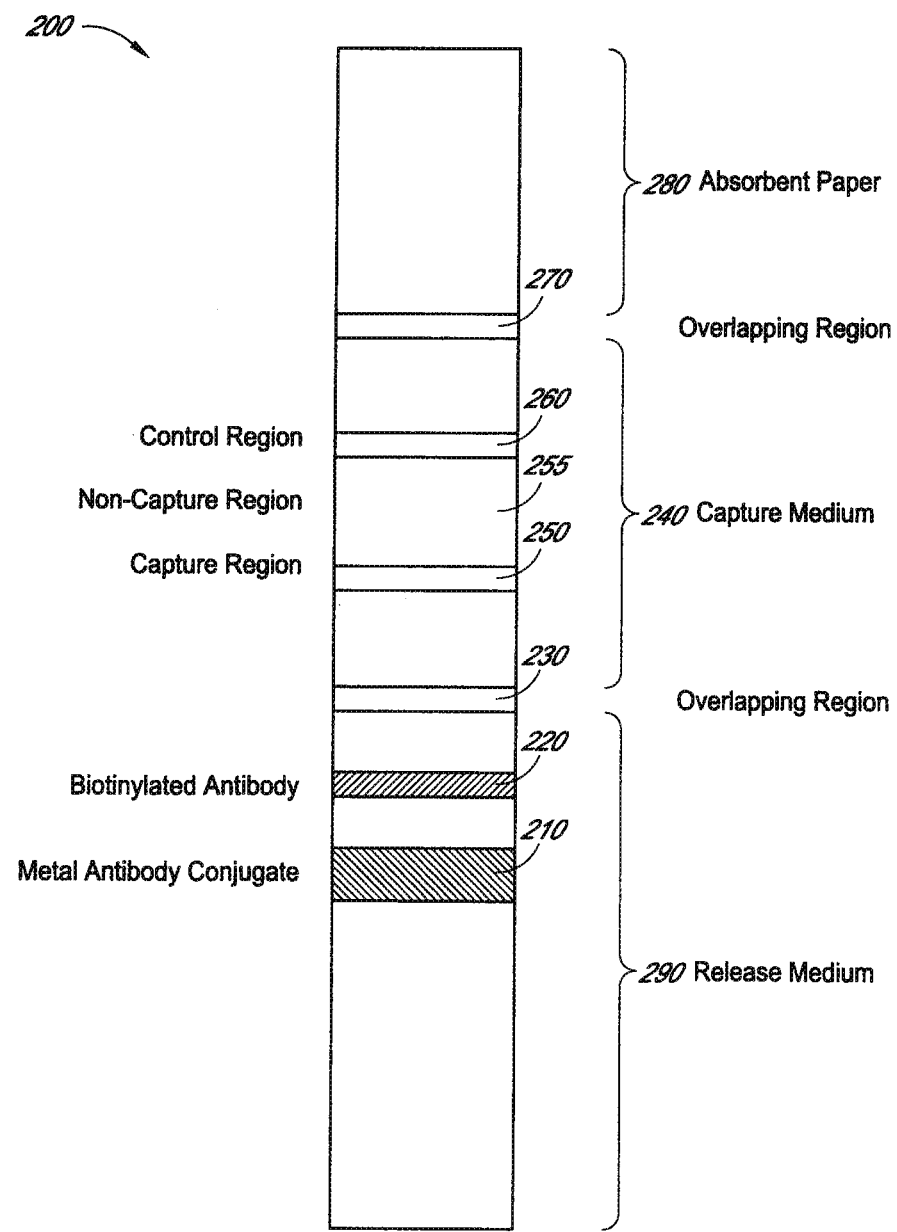
FIGS. 2A-2B show different views of an embodiment of a test strip that may be in a drying-dependent impedance-based assay device.

The methods and devices described herein are used to perform immunologically-based diagnostic tests. The devices described herein enable a user to determine with high accuracy and sensitivity the presence or absence of a biological marker which is indicative of a physiological condition or state. For example, the methods and devices described herein can enable untrained personnel to reliably assay a liquid sample for the presence of small quantities of a particular analyte, while avoiding false positives and simplifying test procedures. The devices described herein are ideal for use in over-the-counter test kits, which can enable a consumer to self-diagnose, for example, pregnancy, ovulation, venereal disease and other diseases, infections, or clinical abnormalities which result in the presence of an antigenic substance in a body fluid, including determination of the presence of metabolites of drugs or toxins. Some embodiments involve the use of a biphasic chromatographic substrate to achieve an easily readable, sensitive, reproducible indication of the presence of an analyte, such as human chorionic gonadotropin (hCG), follicle stimulating hormone (FSH), thyroid stimulating hormone (TSH) or luteinizing hormone (LH), in a test sample, such as a human urine sample. A variety of analytes can be detected in a variety of liquid samples, including urine, blood, saliva, or any other liquid.

Disclosed herein are drying-dependent, impedance-based methods, systems and devices for detecting and quantifying the presence of an analyte in a fluid sample. The disclosures exploit the difference in the hydroscopic nature between a capture region bound with a metal-labelled antibody and a bare membrane not bound with the metal-labelled antibody. This difference results in the capture region being wetted for longer than the bare membrane after application of a fluid sample. The relative wetness, i.e. dryness, between the capture region and bare membrane as they dry has been found to provide a difference in impedance that lends itself to a simpler and more reliable design of impedance-based assays.

FIGS. 1A-C illustrate different views of an embodiment of an exemplary device 10. FIG. 1A illustrates a perspective view of the device 10 with a cap 14 intact, while FIG. 1B illustrates a perspective view of the device 10 with the cap 14 removed. FIG. 1C illustrates a top view of the device 10 with the cap 14 intact. The device 10 also comprises an outer, molded casing 12 which defines a hollow, elongate enclosure The casing 12 is configured to provide a recessed portion 20 shaped to permit users to place their thumb into the recessed portion and their forefinger on the bottom of the casing to securely hold the device 10. A central section on the top of the casing 12 defines a centrally located window 40 which permits a user to observe displayed test results. Inside the casing 12 is a lateral flow test strip and electronic components, details of which will be described further below. The casing 12 contains a sample receiving member 16 onto which a liquid sample can be applied to the test strip in the device 10. The removable cap 14 can be secured to one end of the casing 12 over the sample receiving member 16. A sample receiving member 16 is positioned so that part of the sample receiving member 16 is received in the enclosure defined by the casing 12 and part of the sample receiving member 16 extends from the end of the enclosure defined by the casing 12.

In some embodiments, changes in impedance are sensed electronically, as is discussed in further detail below, and the results are presented to a user on a display 42. The display 42 may, render various icons or messages to a user, such as test results, device status, error messages, etc. The display 42 may be color or monochrome. In one embodiment, the display 42 is a liquid crystal display (LCD).

FIG. 2A is a top view of a diagram of an, embodiment of a triphasic test strip suitable for use in an implementation of the invention, although it will be appreciated that a wide variety of test strip designs may be used. The fluid path along the test strip 200 will be discussed starting with the bottom of FIG. 2A as shown and moving up. This spatial orientation is merely a convenience for the sake of description.

At the bottom of the test strip 200, a fluid sample may be applied to the strip's release medium 290. The test strip 200 may be formed from an absorbent material to aid in the uptake of the fluid sample. The fluid sample may flow across the strip and encounter a conjugate region 210. In the embodiment shown, the conjugate region 210 is a colloidal gold antibody conjugate region where the antibody binds to the analyte of interest (e.g. LH) present in the fluid sample. As the fluid sample passes through the conjugate region 210, analyte in the fluid sample will bind the gold-conjugated antibody in the liquid phase and carry the conjugate-analyte complex along the strip. While the embodiments shown are in the context of antibodies conjugated with a metal label, other materials may be used. In some embodiments, polymers are used as the label. For instance, PEG-alated systems or dendrimers may be used as a label.

The fluid sample may then flow through a second antibody region 220. In the embodiment shown, the second antibody region 220 includes biotinylated antibody that specifically binds to a different epitope on the analyte of interest than the gold-conjugated antibody, forming a "sandwich" of analyte and two antibodies one antibody with colloidal gold and the other with biotin. The sandwich may then be carried further along the test strip across a first overlapping region 230. The area from the start of the test strip 200 to the first overlapping region 230 may generally be referred to as the release medium 290.

After or at the overlapping region 230, the fluid on the test strip 200 encounters a capture medium 240, which may be nitrocellulose, or the like. As the fluid sample continues along the test strip 200 in the capture medium 240, the sample may next encounter a capture region 250, which may be a test line, containing a capture agent. The capture region 250 may be a narrow or wide region spanning all or substantially all of the width of the strip 200. In some embodiments, the capture agent in the capture region 250 is avidin. The avidin is for binding the biotin on the second antibody to trap the sandwich (with the gold) at the capture region 250. The capture region 250 may become darker as more of the sandwich complexes are accumulated.

In an example implementation where the conjugate comprises colloidal metal such as, for example, gold or silver, an electrical system including electrodes and a processor (not shown in FIG. 2A) may measure effects such as hydroscopic effects, of the colloidal gold specifically bound at the capture region 250 of the test strip 200. The processor may perform a transformative algorithm on the electrical signals detected by the electrodes. As is discussed in further detail herein for example with respect to FIGS. 3A-3C and 4A-4G, the electrodes may be in a number of different configurations, including on the strip 300 itself or on a circuit board that is assembled so the electrodes make contact with a conductive area around the capture region 250, and the processor may use electrical signals detected by the electrodes to measure a drying-dependent impedance associated with the capture region 250.

After the capture region 250, the test strip 200 includes a non-capture region 255. The non-capture region 255 is a region of bare membrane material of the strip 200 across which a drying-dependent impedance is measured. The non-capture region 255 is shown unmarked. However, the non-capture region 255 may be indicated by one or more lines, similar to the embodiment of the capture region 250 as shown. In some embodiments, the non-capture region 255 is bare membrane. The bare membrane region need not be a line shape, but may also be a strip or any shape. The region 255 may further be located anywhere along the length of the strip 200, bare membrane or otherwise, where there is no capture agent or striping reagent. The non-capture region 255 may thus be below the capture region 250 on the strip 200 (as oriented in FIG. 2A), such that the fluid sample encounters the non-capture region 255 before the capture region 250.

Electrodes (not shown in FIG. 2A) may be positioned in proximity to the non-capture region 255. The electrodes detect electrical signals to be used by the processor to measure a drying-dependent impedance across the non-capture region 255. As is discussed in further detail herein, for example with respect to FIGS. 3A-3C and 4A-4G, the electrodes may be in a number of different configurations, including on the strip 300 itself and/or on a circuit board that is assembled so the electrodes make contact with a conductive area around the capture region 250, and impedance measurements from electrodes in the capture region 250 and the non-capture region 255 as the respective regions dry may be used to detect analyte presence and/or quantify analyte amount in the fluid sample.

After the capture region 250 and non-capture region 255, the test strip 200 may include a control region 260. The control region 260 may also generally be referred to as a reference region or reference line. When present, the control region 260 includes antibodies or other proteins that specifically bind the gold-conjugated antibody to provide a measurement of gold-bound antibody in the fluid that is not specifically bound to the analyte. Impedance measurements from the capture region 250 and/or control region 260 may be used separately to define successful testing. Strips without a control region 260 may be advantageous because it eliminates the need for the antibodies at this region as well as reduces complexity of the electrical system, thus reducing cost of the strip.

In embodiments with a control region 260, electrodes (not shown in FIG. 2A) may be positioned in proximity to the control region 260. The electrodes detect electrical signals to be used by the processor to measure an impedance across control region 260. As is discussed in further detail herein, for example with respect to FIGS. 3A-3C and 4A-4G, the electrodes may be in a number of different configurations, including on the strip 300 itself and/or on a circuit board that is assembled so the electrodes make contact with a conductive area in and/or around the capture region 250.

In some embodiments measurements from multiple non-capture, capture and/or control regions 255, 250, 260 on the same strip 200 may be taken. Therefore, there may be multiple sets such as pairs, of electrodes in each or in some of the regions 255, 250, 260. Such configurations may reduce the chances of false negatives by sampling over a larger area. This may also mitigate the effects of localized abnormalities, defects or other causes of changes to the strip drying properties that may, for instance, be introduced during the preparing, making and/or life of the strip.

The capture medium 240 may interface with a second overlapping region 270. The second overlapping region 270 may serve as a border between the capture medium 240 and an absorbent portion 280 of the test strip. The absorbent portion 280 of the test strip 200 facilitates the uptake of the fluid sample as it arrives at the end of the test strip 200.

The various overlapping regions 230, 270 may be in a number of different configurations. For instance, the release medium 290 may be on top of the capture medium 240 at the overlapping region 230, or vice versa. Similarly, the capture medium 240 may be on top of the absorbent portion 280 at the overlapping region 270, or vice versa. Still other configurations of the overlapping regions 230, 270 within the ordinary skill of the art are contemplated and are within the scope of the present disclosure.

Figure 2B:
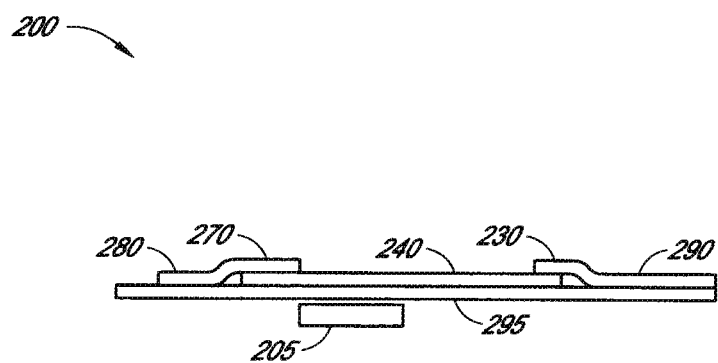

FIG. 2B is a side view of an embodiment of a triphasic test strip 200. The strip 200 has a mylar backing 295. The release medium 290 is, coextensive with an end of the mylar backing 295. The release medium 290 overlaps with a portion of the capture medium 240 at overlapping region 230. An opposite portion of the capture medium 240 overlaps with the absorbent paper 280 at overlapping region 270. While the capture medium 240 is shown underneath the release medium 290 and absorbent paper 280, it may also be on top, or combinations thereof.

Further shown in FIG. 2B is a drying mechanism 205. The drying mechanism 205 facilitates drying of the capture medium 240. It may be positioned over the capture region 250, the non-capture region 255 and/or the control region 260, or combinations thereof. The drying mechanism 205 may further be located in any other positions of the capture medium 240 and/or strip 200, such as the release medium 290 and absorbent paper 280. As shown, the drying mechanism 205 is under the mylar backing 295.

The drying mechanism 205 may be a single component or multiple components. Further, the drying mechanism 205 may be of various sizes and shapes. For instance, it may span the width of the strip 200 or a potion thereof, and it may be of various lengths along the long dimension of the strip 200. It may also be positioned in various locations. For instance it may be centered with respect to the width of the strip, or it may be off-center.

The drying mechanism 205 may be passive or active. In some embodiments, the drying mechanism 205 is a valve that allows in ambient air. The valve may have a fan or other mechanism to actively bring air in and/or through the device 10. In some embodiments, the drying mechanism 205 is a drying element. For instance, it may be a heating element. In some embodiments, the drying mechanism 205 is a mechanical press. For instance, it may be a sponge or other material capable of absorbing moisture or otherwise drying the strip 200. The drying mechanism 205 may further have moveable parts. For example, a valve, fan, element, heater, press, sponge or any other embodiment may move to dry the strip 200. In some embodiments, a mechanical press, is pressed to the strip 200 with varying pressures for varying amounts of time.

Figure 3C:
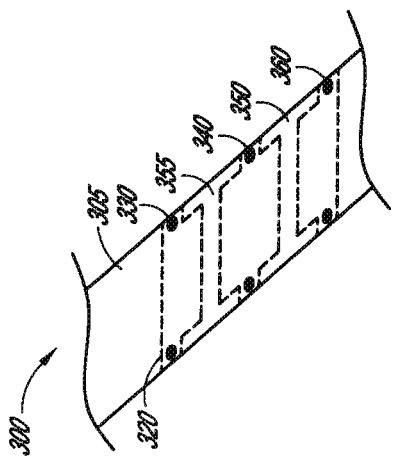
FIG. 3C shows a partial perspective view of an embodiment of a circuit board with electrodes that may be used with the test strip of FIG. 3B.
Figure 3B:
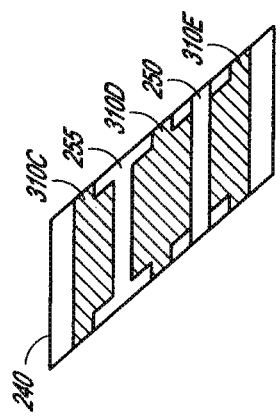
FIGS. 3A-3B show perspective views of various embodiments of test strips that may be in a drying-dependent impedance-based assay device.
Figure 3A:
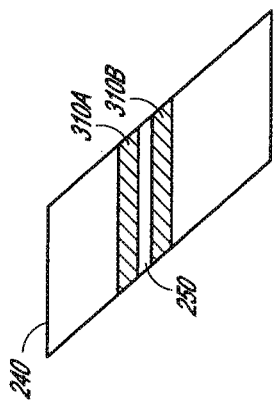

FIGS. 3A-3B show perspective views of various embodiments of conductive areas about measurement regions on a test strip that may be used in a drying-dependent impedance-based assay device. Referring to FIG. 3A, the capture medium 240 is shown having the capture region 250. The capture region 250 may span the entire width of the capture medium 240. In some embodiments, the capture region 250 may span less than the entire width of the capture medium 240. On, both sides of the capture region 250 may be conductive areas 310A, 310B. The conductive areas 310A, 310B may be areas of the strip 200 adjacent to or otherwise near a measurement region, such as the capture region 250 or the like, with enhanced conductivity. In some embodiments, the conductive areas 310A, 310B may be adjacent to or otherwise near the non-capture region 255 and/or the control region 260.

The conductive areas 310A, 310B may include a variety of conductive materials. In some embodiments, the conductive areas 310A, 310B are screen printed materials. For instance, the conductive area may be a screen printed electrode, mesh, film or membrane. In some embodiments, the conductive areas 310A, 310B are a screen printed electrode based on carbon, gold, platinum, silver, carbon nanotubes ink, or combinations thereof. In some embodiments, the conductive areas 310A, 310B include carbon black, or variations thereof.

In related aspects, the conductive areas 310A, 310B may be in contact with electrodes from other parts of the device 10. For instance, when the device 10 is assembled, electrodes from a circuit board (e.g. a printed circuit board, or the like) may be in contact with the conductive areas 310A, 310B to measure impedance across the capture region 250.

FIG. 3B shows an exemplary embodiment of conductive areas about two measurement regions on a test strip. As shown, the capture medium 240 has the capture region 250, the non-capture region 255 and three conductive areas 310C, 310D, 310E. The conductive areas 310C, 310D, 310E may be in between and/or on either side of the two measurement regions. As shown, a first conductive area 310C is adjacent to the non-capture region 255, a second conductive area 310D is in between the capture region 250 and the non-capture region 255, and a third conductive area 310E is adjacent to the capture region 250.

The various conductive areas 310A-E may have various shapes and sizes. As shown in FIG. 3A, the conductive areas 310A, 310B may be rectangular and span the entire width of the capture medium 240. As shown in FIG. 3B, the conductive areas 310C, 310D, 310E may span the entire width of the capture medium 240 but have notches, or the like. For example, the notches may be adjacent to the measurement regions, i.e. the capture region 250 and the non-capture region 255. Having notched regions of the various conductive areas may facilitate reducing noise and similar effects due to non-uniformities of the strip near the edges. Other shapes of the various conductive areas may further be implemented (e.g. depending on the particular application) and are within the scope of the present disclosure.

FIG. 3C shows a partial perspective view of an embodiment of a circuit board or substrate with electrodes that may be used with the test strip of FIG. 3B. Other configurations of boards or substrates may be used with test strips, such as that shown in FIG. 3A. As shown in FIG. 3C, a portion of a circuit board 305 is visible having various electrodes 330, 340, 360, and others. The electrodes 330, 340, 360 may be a variety of types having different sizes, shapes, configurations, orientations, etc. For example, the electrodes 330, 340, 360 may be pins, pads, membranes, etc. The electrodes 330, 340, 360 may be in a pattern. In related aspects, the pattern may be complementary to the layout of the capture region 250, non-capture region 255, and/or the various conductive areas, such as those on the capture medium 240 as shown in FIG. 3B. Dotted lines 320 in FIG. 3C outline the various regions that match various conductive areas of the capture medium 240 in FIG. 3B. As shown in FIG. 3C, the dotted lines 320 define a non-capture outline 355 (which matches the shape of non-capture region 255) as well as a capture outline 350 (which matches the shape of the capture region 250). The dotted lines may further define regions that match up with the conductive areas 310C, 310D, and/or 310E. The pattern of electrodes may be based on these various areas defined by the dotted lines 320. A first electrode 330 and second electrode 340 are located adjacent to the non-capture outline 355 in locations that would match up with corresponding first and second conductive areas 310C and 310D on the strip 200. Similarly, a third electrode 360 is located adjacent to the capture outline 350 in locations that would match up with corresponding third conductive area 310E on the strip 200.

When the board 305 of FIG. 3C contacts the capture medium 240 of FIG. 3B, the electrodes 330, 340, 360 may each be located, oriented, positioned or otherwise configured to contact a respective conductive area 310C, 310D, 310E on the capture medium 240. Thus, the impedance may be measured across the various measurement regions using conductive pathways that are formed from the conductive areas 310C, 310D, 310E to one of the respective contacting electrodes 330, 340, 360. Because the conductive areas 310C, 310D, 310E abut the measurement regions, the signal is indicative of the impedance across the measurement region. In some embodiments, the board 305 of FIG. 3C is turned over and placed on top of the capture medium 240 as shown in FIG. 3B. Further, other electrodes are shown in FIG. 3C which may be used instead of or in addition to electrodes 330, 340, and 360. In some embodiments, multiple measurements across the measurement meurement region are taken for enhanced accuracy and reliability of impedance results.

FIGS. 3A-3C demonstrate embodiments for measuring the impedance as across the measurement regions with electrodes that are brought to contact with conductive areas on the strip. However, other embodiments include electrodes embedded in the test strip 300 that would then be connected to the circuit board 305. Regardless of whether the electrodes are part of the board 305 and brought into contact with the strip 300 when assembled, tr or whether the elecodes are embedded in the strip 300, the electrodes may have numerous layouts and patterns and be of varying shapes, sizes and orientations. Some of the possible layouts and designs for the electrodes are discussed with respect to FIGS. 4A-4G.

FIGS. 4A-4G show other embodiments of layouts 400 of electrodes 430, 440 in the proximity of a measurement region 420 on a strip portion 410 that may be implemented in a test strip 200 in a drying-dependent impedance-based assay device 10. In some embodiments, the strip portion 410 may be the capture medium 240 of FIGS. 2A, 2B, 3A, and/or 3B. The measurement region 420 may, be the capture region 250, the non-capture region 255 and/or the control region 260. While FIGS. 4A-4G show embodiments of the electrode layouts on a strip portion 410, it is understood that the layouts shown and discussed below may also be embodied on the board 305 (see FIG. 3C). Thus, the electrode layouts discussed in the context of being embedded in on or with the strip portion 410 may also be in embodiments where the electrodes are on a circuit board and are brought into contact with the conductive areas 310 (see FIGS. 3A-3B).

FIGS. 4A and 4B show layouts 400 of electrodes 430, 440 as bands or wires that span all or substantially all of the width of the strip portion 410 near the measurement region 420. The electrodes 430, 440 may, be less wide, for example a wire, or more wide, for example a band. As shown in Fla 4A, the electrodes 430, 440 may be respectively below and above the measurement region 420. Electrode 440 is on top of the strip portion 410 over the measurement region 420, while electrode 430 is below the strip portion 410 under the measurement region 420. As shown in FIG. 4B, the electrodes 430, 440 may be on either side or edge of the measurement region 420. Electrode 440 is on one side of the measurement region 420, while electrode 430 is on the opposite side of the measurement region 420. The electrodes 430,440 need not be near either side of the measurement region 420, but rather the electrodes 430,440 may be away from one or, both sides of the measurement region 420.

FIGS. 4C and 4D show layouts 400 of electrodes 430, 440 as pin electrodes near the measurement region 420. The electrodes 430, 440 may be configured on top, through, or partially through the strip portion 410. As shown in FIG. 4C, the electrodes 430, 440 may be on either side of the measurement region 420. Electrode 440 is on one side of the measurement region 420, while electrode 430 is on the opposite side of the measurement region 420. As shown in FIG. 4D, the electrodes 430, 440 may be configured along the measurement region 420. Electrode 440 is on one end of the measurement region 420, while electrode 430 is on the opposite end of the measurement region 420.

FIG. 4E shows a layout 400 of electrodes 430, 440 as interdigitated electrode arrays having electrode teeth 435, 445 that span all or substantially all of the width of the strip portion 410 near the measurement region 420. Interdigitated electrode arrays may be used to improve the signal to noise ratio. The teeth 435, 445 of array electrodes 430, 440 may be micro- or macro-scale. The electrodes 430, 440 and/or electrode teeth 435, 445 may span less than the width of the strip portion 410. As shown, the electrodes 430, 440 may be respectively below and above the measurement region 420. Electrode 440 is on top of the strip portion 410 over the measurement region 420, while electrode 430 is below the strip portion 410 under the measurement region 420.

FIG. 4F shows a slayout 400 of electrodes 430, 440 as comb electrodes that span all or substantially all of the width of the strip portion 410 through the measurement region 420. The electrodes 430, 440 may be arrays of pins mounted through the measurement region 420 from either side of the strip portion 410. The electrodes 430, 440 may span less than the width of the strip portion 410. As shown, the electrodes 430, 440 may be respectively below and above the measurement region 420. Electrode 440 is on top of the strip portion 410 over the measurement region 420, while electrode 430 is below the strip portion 410 under the measurement region 420.

FIG. 4G shows a layout 400 of electrodes 430, 440, 450, 460 as pin electrodes both near and away from the measurement region 420. The electrodes 430, 440, 450, 460 may be pins or bands. Polling different pairs of the electrodes 430, 440, 450, 460 allows for simpler manufacturing as the measurement region 420 does not require precise placement on the strip portion 410. It also allows for improved measurements through algorithms that analyze data from different pairs of the electrodes 430, 440, 450, 460. Some embodiments may have multiple measurement regions 420 each with one or more electrodes.

Figure 5:
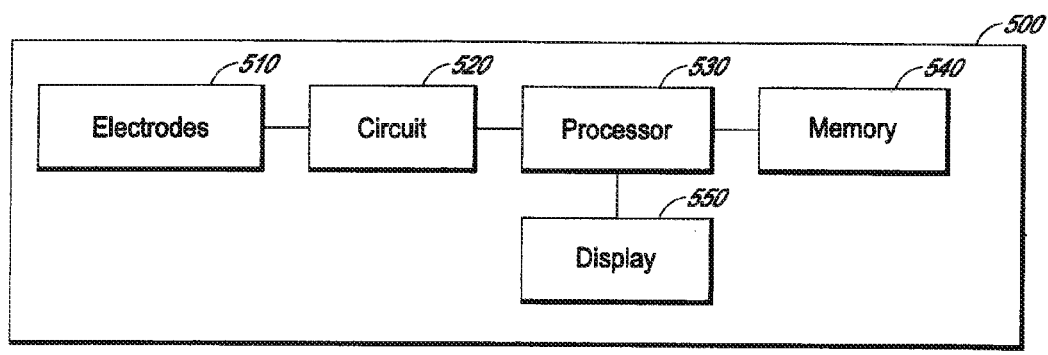
FIG. 5 shows a block diagram of an embodiment of an electrical system that may be in a drying-dependent impedance-based assay device.

The electrodes associated with the strip portion 410 and strip 200 may be integrated with an electrical system and processor to produce and analyze measurements of impedance in the various measurement regions 420. FIG. 5 shows a block diagram of an embodiment of an electrical system 500 that may be in a drying-dependent impedance-based assay device 10. The system 500 includes electrodes 510. The electrodes 510 are conductive materials associated with the measurement regions 420 and connected to a circuit 520. The circuit 520 transmits electrical signals to a processor 530. The processor 530 analyzes the signals in order to measure the impedance of the regions 420. The processor 530 is also connected to a memory 540. The memory 540 may contain a set of instructions for the processor 530 to carry out in order to measure the impedance. The memory 540 may also store other digital data, such as records of impedance measurements, data correlations, lookup tables, etc. The processor 530 is also connected to a display 550. The processor 530 may send signals to the display 550, which may be a digital display, in order to show information related to the various processes performed. For instance, the display may indicate a power status of the device 10, that a measurement is currently being taken, or the results of a measurement such as the presence and/or quantity of an analyte, or the non-presence of an analyte, in a fluid sample.

Figure 6:
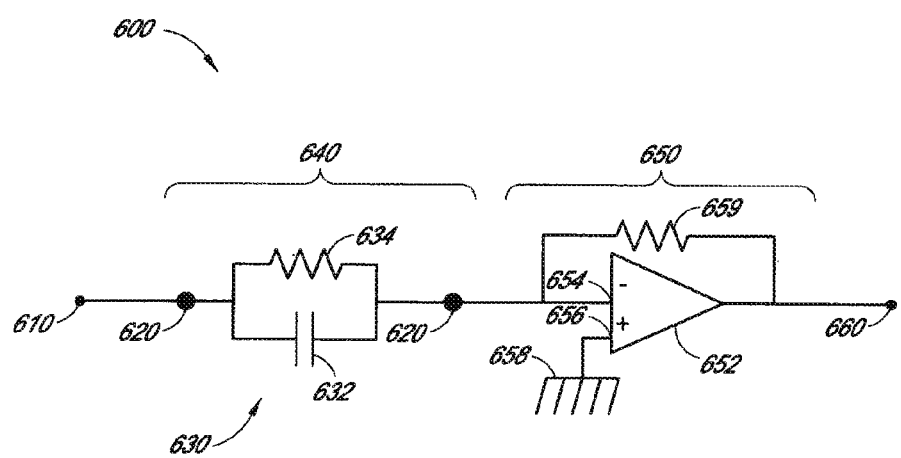
FIG. 6 shows a circuit diagram of an embodiment of a circuit that may be in a drying-dependent impedance-based assay device.

The circuit 520 and electrodes 510 of FIG. 5 may be implemented in a number of configurations in a device 10. FIG. 6 shows a circuit diagram of an embodiment of a circuit 600 including electrodes 620. As shown, the circuit 600 includes a strip region 640 that may be, for example, the measurement region 420 across the strip 410 of FIGS. 4A-4G. In FIG. 6, a voltage may be applied to the circuit 600 with a voltage source at node 610. The voltage may be applied over a range of frequencies. In some embodiments, the range is 1 KHz to 100 KHz. Current flows through the circuit 600 to the first electrode 620 in the strip region 640.

After first electrode 620, current flows through the strip region 640 and to a second electrode 620. The strip region 640 is represented as an RC circuit 630 with a resistor 634 and capacitor 632 in parallel. The amount of current flowing to the second electrode 620 will vary depending on the impedance of the strip region 640. The impedance is a measure of the opposition that the strip region 640 presents to the current flowing through it. If the impedance is high, less current will flow through the strip region 640, and vice versa. Thus other related electrical concepts are applicable to and may be measured, in the present disclosure, such as resistance and capacitance.

The amount of impedance is indicative of the hydroscopic state of the strip region 640. If the strip region 640 is wet, there will be less oppositions to the current as compared to if the strip region 640 was dry. Thus the impedance of a wet region will be low relative to a dry region. Conversely, a relatively dryer strip region 640 will present more opposition to the current, and thus the impedance will be high relative to if the region 640 was wet.

Further, the presence or absence of colloidal metal in the strip region 640 influences the change in the hydroscopic state of the region 640 over time. For example, if capture region 250 and non-capture region 255 are both wet from a fluid sample, where capture region 250 has captured metal, then capture region 250 will dry at a different rate than non-capture region 255. In such a case, capture region 250 will be wetted longer than the non-capture region 255. Thus, the capture region 250 and non-capture region 255 will provide differences in impedance as the regions dry.

After flowing through the strip region 640, the current encounters the second electrode 620. The second electrode 620 is connected to a current to voltage converter 650, to which the current next flows. The convertor 650 includes an operational amplifier or op-amp 652 and a feedback resistor 659. The op-amp 652 has a non-inverting input 654 and inverting input 656 connected to a ground 658. The current flows to the converter 650 and is output as a voltage at node 660. The output voltage at node 660 compared to the input voltage at node 610 provides a measurement of the impedance associated with the strip region 640. And, as mentioned, the impedance is indicative of the hydroscopic state of the strip region 640, which in turn is indicative of the presence and quantity of analyte in the region 640.

Figure 7:
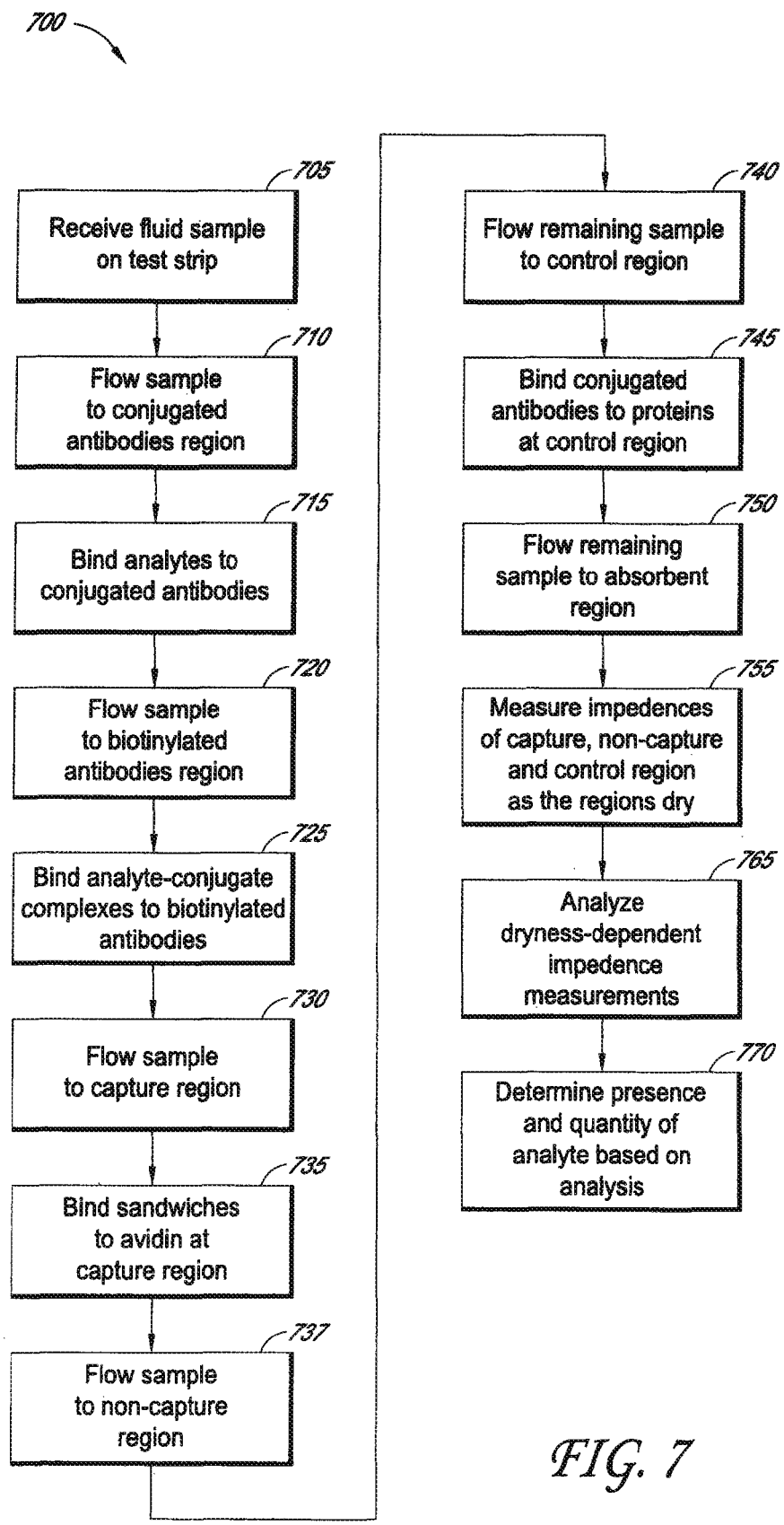
FIG. 7 shows a flow chart of an embodiment of a method of measuring drying-dependent impedance in a lateral flow assay device to determine the presence and quantity of an analyte.

FIG. 7 shows a flow chart of an embodiment of a method 700 of measuring drying-dependent impedance in the device 10 to determine the presence and quantity of the analyte in the fluid sample. The process begins with step 705 where a fluid sample is received on a test strip. The fluid sample may be received at the sample receiving member 16 or release medium 290. Next, in step 710, the fluid sample flows to a conjugate antibodies region, which may be the conjugate region 210. At the conjugate antibodies region, analytes in the fluid sample, if present, are bound to the conjugated antibodies in the next step 715. The fluid sample then flows to a biotinylated antibodies region, which may be the second antibody region 220. At the biotinylated antibodies region, the analyte-conjugate complexes are bound to the biotinylated antibodies in step 725. Thus a "sandwich" of analyte and two antibodies, one with colloidal gold and the other with biotin, are formed and continue flowing along the strip. Next, in step 730, the fluid sample flows to a measurement region or test line, which may be the capture region 250. En route to the test line, the sample may encounter an interface between the release medium and the capture medium, such as the overlapping region 230. At the test line, the sandwiches in the fluid sample are bound to avidin and captured at the test line. In some embodiments, the method 700 then moves to step 740 wherein the fluid sampled flows to a control line, such as the control region 260. Then, in step 745, conjugated antibodies are bound to proteins at the control line. From the control line, the remaining fluid sample in step 750 flows to the absorbent region.

The process 700 also involves various steps related to measuring and analyzing electrical signals from electrodes on the strip. It is understood that these steps are not necessarily performed after steps 705-750. The remaining steps may be done before, during and/or after steps 705-750. Therefore, the discussion of, any steps in a particular order does not imply an order with respect to carrying out the steps of process 700.

In step 755, the impedance is measured of the test line and a non-capture region, which may be respectively capture region 250 and non capture region 255. The impedance of the test line may be measured, for example, using electrodes 340, 360, and the impedance of the non-capture region may be measured, for example, using electrodes 330,340. The impedances are measured as the various lines or regions dry. In step 755, the impedance of the control line may also be measured. In step 765, the impedance measurements of the test line and non-capture region are analyzed. In step 770, the presence and/or quantity of an analyte in the fluid sample is determined based on the analysis of the impedance measurements.

The analysis of impedance measurements of the capture and non-cap ure regions to determine the presence and/or quantity of an analyte involves analyzing the differences in those measurements as the two regions dry. Certain characteristics of the resulting differences may be used in the analysis, such as the magnitude of the impedance difference. A threshold impedance difference may be identified experimentally whereby a test impedance difference is compared to the threshold. For instance, a test impedance difference that is more than a threshold impedance difference may indicate the presence of an analyte in the fluid sample. The test impedance difference may be defined in a number of ways. For example, the test impedance difference may be the difference of the two regions as a percentage of the impedance of the non-capture region at any given point in time. Thus, the threshold impedance would be defined as a percentage, and the impedance difference would then be compared to this threshold percentage. Other characterizations of the impedance difference known in the art may be used and are within the scope of this disclosure.

Figure 8A:
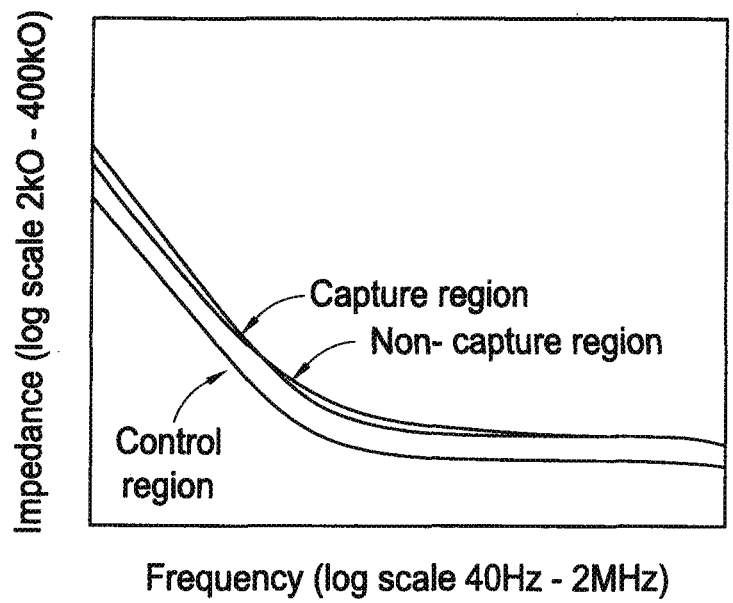
FIGS. 8A-8C show graphs displaying various results of impedance measurements for a capture region and a non-capture region.
Figure 8B:
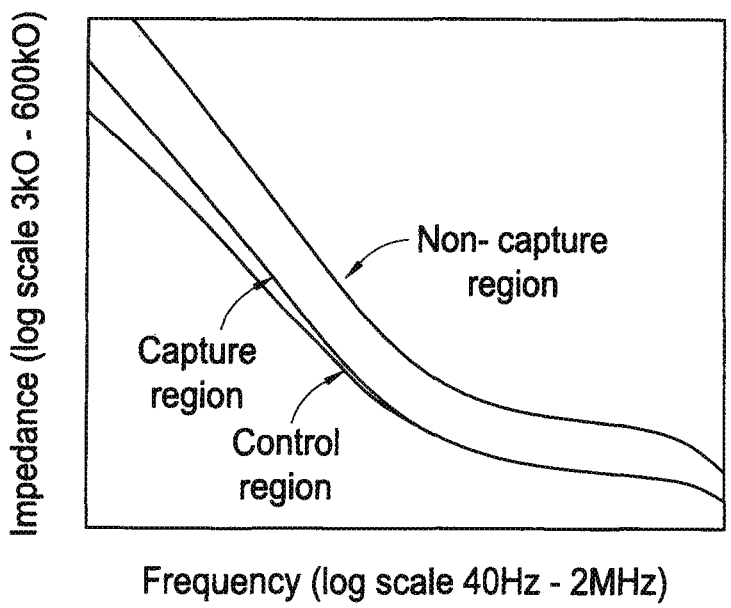
Figure 8C:
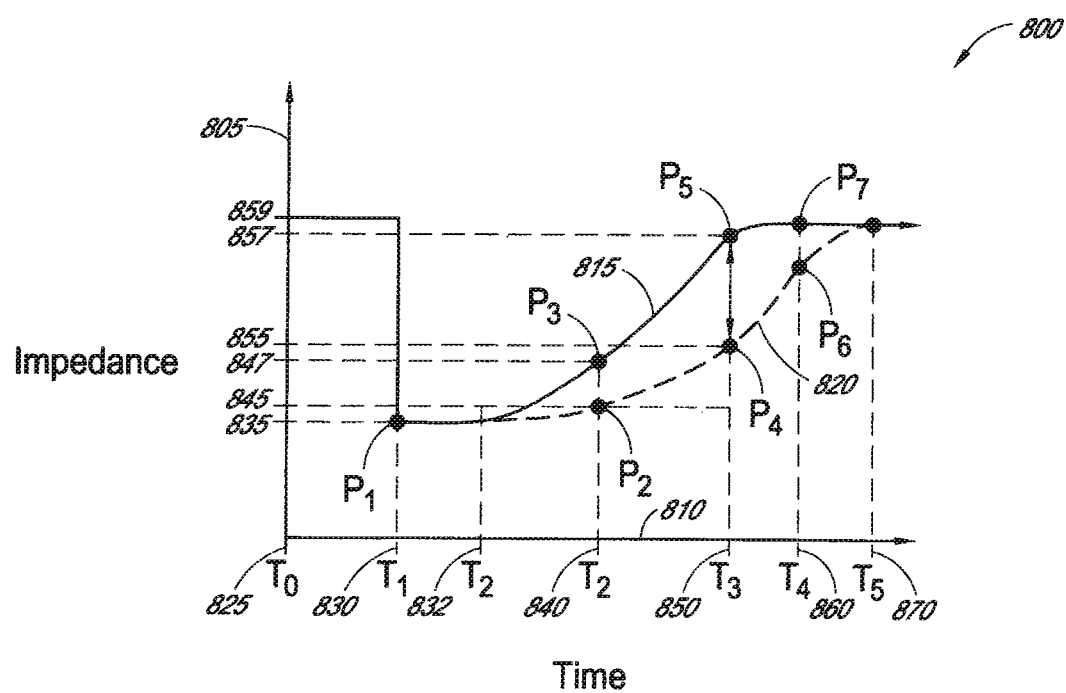

FIGS. 8A-8C show graphs displaying various results of impedance measurements and the differences for a capture region and anon-capture region. FIGS. 8A and 8B show impedance values on a log scale measured at various frequencies for a semi-dry strip with no analyte and with analyte, respectively. The strip may be semi-dry as defined with respect to a drying time period, which is discussed in more detail below. FIG. 8C shows impedance values for a capture region and a non-capture region as the regions dry over time.

Referring to FIGS. 8A and 8B, the impedance values of the capture region, non-capture region and the control region at various sampling frequencies are shown. Without any analyte, the capture region and non-capture region are very similar, as shown in FIG. 8A. However, as shown in FIG. 8B, with analyte the capture region has diverged from the non-capture region. With analyte, in some embodiments the capture region may be closer to the control region values than the non-capture values. The divergence of the capture and non-capture values may be compared to a threshold to determine the presence and quantity of an analyte. For instance, a divergence that is greater than a threshold amount may indicate the presence of an analyte.

As mentioned, the capture region will be wetted for longer if it has captured metal, and thus the impedance difference with the non-capture region will exhibit a certain relationship over time, such as that shown in FIG. 8C. As shown, the vertical axis 805 is the value of impedance, increasing from bottom to top. The horizontal axis 810 is time, increasing from left to fight. Measurements for the impedance of the non-capture region are shown by line 815 and for the capture region by line 820.

At time 825, both regions are dry and have similar impedance values. The values may be the same, as shown at impedance value 859, or they may be, slightly different. The two regions are wetted by the fluid sample at time 830. It is assumed, for simplicity, that the two regions are wetted simultaneously. However, the capture region may be wetted before or after the non-capture region. Because the regions are wet at time 830, the impedance drops to value 835. After time 830, the two regions are drying. At time 832, the impedance measurements of, the two regions diverge. After time 832, the non-capture region values are higher, than the capture region values, as line 815 is higher than line 820. For instance, at time 840, the non-capture line 815 is at point P3 corresponding to impedance value 847, while capture line 820 is at lower point P2 corresponding to lower impedance value 845. At time 840, the difference between point P2 and P3 as a percentage of the non-capture impedance at point P3 may be 25%. If this is above a pre-determined threshold difference, then the sample may contain analyte.

After time 840, the capture and non-capture values continue to diverge until a maximum divergence occurs at time 850. At time 850, the non-capture line 815 is at point P5 corresponding to impedance value 857, while capture line 820 is at lower point P4 corresponding to lower impedance value 855. After time 850, the lines 815, 820 begin to converge, indicating that the difference in impedance between the two regions is decreasing. For instance, at time 860, the non-capture line 815 is at point P7 corresponding to impedance value 830, while capture line 820 is at lower point P6 corresponding to a lower impedance value. The difference between P7 and P6 is smaller than the difference between P5 and P4, which is larger than the difference between point P3 and P2. Thus, the impedance differences are diverging before time 850 and converging afterward, and therefore the impedance difference between the two regions at time 850 is at a maximum.

As shown, the magnitude of the impedance difference may vary over time. Thus, the impedance differences are measured for a sufficient amount of time after the regions are wetted, i.e. as they dry. This adds confidence to the determination by reducing the chance of a false negative. This time period may be designated as a drying time period. The length of the drying time may be determined based on the relative values of the impedance differences over time. For instance, the drying time may be defined as a length of time sufficient for the test impedance difference to reach a maximum. In FIG. 8, this would be up until time 850. This time 850 would be determined as a time rof maximum impedance difference by measuring for a time after time 850. Since the measurements after time 850 will show a decreasing difference in impedance, then it is determined that time 850 was a time of maximum impedance difference. The drying time period may also be used to measure the impedance differences with other analyses, for example that discussed above with respect to FIGS. 8A and 8B.

Another characteristic that may be used in the analysis is the rate of drying. The drying rate, of the capture region may be indicative of the quantity of analyte in the fluid sample. A correlation between the drying rate and analyte quantity may be determined experimentally, and a test drying rate may be compared to this correlation to determine the analyte quantity in the fluid sample. Referring to FIG. 8C, the drying rate of the capture region may be determined by calculating the slope of line 820 at a given point in time. Relatively flatter portions of line 820, such as point P2, will have a smaller slope than steeper portions, such as at point P4. Thus the drying rate at point P2 is less than the rate at point P4. In this manner, an instantaneous rate of change of the drying may be determined. A drying rate over a period of time may also be determined. In some embodiments, the drying rate over a period of time may be determined by comparing two data points at different times. For instance, for the capture region impedance values shown by line 820, the impedance value 845 at point P2 corresponding to time 840 may be subtracted from the impedance value 855 at point P4 corresponding to later time 850. This difference may then be divided by the difference in time between time 850 and time 840, to yield a rate of change in drying over, the time period from time 840 to time 850. Further, a similar rate of change may be determined for the non-capture region using line 815 and values of impedance at the corresponding times 840, 850, by using data points P3, P5 and corresponding impedance values 847, 857. The drying rates, whether instantaneous or over a period of time, can then be compared between the capture and non-capture regions. These and other drying rates, or the differences between, drying rates for various regions, may then be compared with pre-determined correlations of drying rate, or differences in drying rates, and analyte quantity.

In some embodiments, analysis of the drying rate over a larger period is used. In some embodiments, the amount of time for the impedance difference to reach a threshold amount may be used. For instance, for a given threshold, a correlation may be found experimentally between the length of time for the test difference to reach this threshold and the amount of analyte. For example, a threshold impedance difference may be chosen as 10%, and a correlation may be determined between the time it takes for a test difference to reach 10% and the quantity of analyte. Referring to FIG. 8C, the difference between points P7 and P6 may be 10% of the impedance at point P7. Thus, the period from time 832 when the impedances diverge, to time 860 when the impedance difference equals the threshold amount, may be correlated to an analyte quantity based on the pre-determined correlation. It is noted that the difference, so defined, may also be 10% while the test differences are diverging, for instance, at time 840. Therefore, other variables may be used in the algorithms employed by the processor in analyzing the rate, such as only using differences after a maximum difference has been reached.

In some embodiments, analysis of an overall drying rate is used. For instance, a correlation may be found experimentally between the analyte quantity and the length of time for the test difference to diverge and then converge again. In FIG. 8C, this may be the period from time 832 to 870. This length of time may be correlated to an analyte quantity based on the pre-determined correlation for an overall drying rate.

Other variations, subsets, correlations and attributes of the drying rate may be used. Further the drying rates may be determined experimentally and correlated for particular materials, molecules, configurations, etc. that may be embodied in the devices and methods disclosed herein. The correlations may also be determined or particular atmospheric conditions such as humidity. Thus, the device 10 may include a sensor to measure the amount of moisture in the air in order to consult the appropriate correlation.

Although this invention has been disclosed in the context of certain embodiments and examples, will be understood by those skilled in the art that the present invention extends beyond the specifically disclosed embodiments to other alternative embodiments and/or uses of the invention and apparent modifications and equivalents thereof. In addition, while a number of variations of the invention have been shown and described in detail other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

The logical blocks, modules and flow chart sequences are illustrative only. A person of skill in the art will understand that the steps decisions, and processes embodied in the flowcharts described herein may be performed in an order other than that described herein. Thus, the particular flowcharts and descriptions are not intended to limit the associated processes to being performed in the specific order described.

Those of skill in the art will recognize that the various illustrative logical blocks, modules and method steps described in connection with the embodiments disclosed herein may be implemented as electronic hardware, software stored on a computer readable medium and executable by a processor, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor reads information from, and writes information to, the storage medium. In the alternative, the storage medium may be integral to the processor. The processor and the storage medium may reside in an ASIC.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others. The scope of the invention is indicated by the appended claims rather than by the foregoing description. All changes which come within the meaning and range of equivalency of the claims are to be embraced within their scope.

A person skilled in the art will recognize that each of these sub-systems may be inter-connected and controllably connected using a variety of techniques and hardware and that the present disclosure is not limited to any specific method of connection or connection hardware.

The technology is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems microprocessor-based systems, a microcontroller or microcontroller based system, programmable consumer electronics, network PCs, minicomputers, mainframe computers, distributed computing environments that include any of the above systems or devices, and the like.

As used herein, instructions refer to computer-implemented steps for processing information in the system. Instructions may be implemented in software, firmware or hardware and include any type of programmed step undertaken by components of the system.

The system may be used in connection with various operating systems such as Linux®, UNIX® or Microsoft Windows®.

The system control may be written in any conventional programming language such as C, C++, BASIC, Pascal, .NET (e.g., C#), or Java, and ran under a conventional operating system. C, C++, BASIC, Pascal, Java, and FORTRAN are industry standard programming languages for which many commercial compilers may be used to create executable code. The system control may also be written using interpreted languages such as Perl, Python or Ruby. Other languages may also be used such as PHP, JavaScript, and the like.

The foregoing description details certain embodiments of the systems, devices, and methods disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being redefined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment may be included with other depicted embodiments in any combination. For example, any of the various components described herein and/or depicted in the Figures may be combined, interchanged or excluded from other embodiments.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims each numerical parameter should be construed in light of the number of significant digits and ordinary rounding approaches.

The above description discloses several methods, devices and systems of the present invention. This invention is susceptible to modifications in the methods, devices and systems. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the following claims.

What is claimed is:

1. A device for detecting an analyte in a fluid sample, the device comprising:
    a strip comprising:
        a sample receiving region configured to receive the fluid sample;
        a capture region;
        a non-capture region; and
        a control region,
            wherein the strip is configured such that when the fluid sample is applied to the sample receiving region, the fluid sample flows laterally to the capture region, the non-capture region, and the control region;
    a plurality of electrodes at least partially aligned with the capture region;
    a plurality of electrodes at least partially aligned with the non-capture region;
    a plurality of electrodes at least partially aligned with the control region; and
    an electronic circuit comprising a processor coupled to the electrodes, the processor configured to execute a set of instructions to perform a method for detecting the analyte in the fluid sample, the method comprising:
        measuring a drying-dependent impedance difference between the capture region and the non-capture region,
        measuring the drying-dependent impedance difference over a drying time period, wherein the drying time period comprises a length of time sufficient for the impedance difference to reach a maximum, and
        measuring impedances of the control region over the drying time period.

2. The device of claim 1, the method further comprising:
    analyzing the impedance difference over the drying time period; and
    determining whether the analyte is present in the fluid sample based in part on the analysis of the impedance difference.

3. The device of claim 1, wherein measuring the drying-dependent impedance difference between the capture region and the non-capture region comprises:
    measuring a first impedance of the capture region;
    measuring a second impedance of the non-capture region; and
    determining a first impedance difference based on subtracting the first impedance from the second impedance.

4. The device of claim 1, wherein the method further comprises:

measuring the impedance difference over a range of frequencies.

5. The device of claim 1, further comprising:
a mechanism for drying the capture region and the non-capture region.

6. The device of claim 1, the strip further comprising:
a first antibody region comprising a first antibody that recognizes an epitope of the analyte; and
a second antibody region comprising a second antibody that recognizes a different epitope of the analyte.

7. The device of claim 6, wherein the first antibody is bound to a first label, and wherein the second antibody is bound to a second label.

8. The device of claim 1, the strip further comprising a release medium, a capture medium, an absorbent medium and a backing.

9. The device of claim 8, wherein the release medium comprises:
the sample receiving region;
a first antibody region comprising a first antibody that recognizes an epitope of the analyte; and
a second antibody region comprising a second antibody that recognizes a different epitope of the analyte.

10. The device of claim 1, wherein the control region comprises antibodies or other proteins that specifically bind a metal-conjugated antibody to provide a measurement of a metal-bound antibody in the fluid that is not specifically bound to the analyte.

11. The device of claim 10, wherein the metal-conjugated antibody is a gold-conjugated antibody and the metal-bound antibody is a gold-bound antibody.

* * * * *